(12) United States Patent
Brown et al.

(10) Patent No.: US 6,769,161 B2
(45) Date of Patent: *Aug. 3, 2004

(54) RADIAL STENT CRIMPER

(75) Inventors: Terry V. Brown, Fridley, MN (US); Andrew J. Dusbabek, Dayton, MN (US); Louis G. Ellis, St. Anthony, MN (US); Scott M. Hanson, Savage, MN (US); Leo M. Klisch, Maple Grove, MN (US); Christopher R. Larson, St. Paul, MN (US); Linda R. Lorentzen Cornelius, Wayzata, MN (US); Justin E. Plessel, Fridley, MN (US); Lawrence W. Ulanowski, Brooklyn Park, MN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/404,986
(22) Filed: Sep. 22, 1999

(65) Prior Publication Data
US 2003/0056360 A1 Mar. 27, 2003

Related U.S. Application Data

(63) Continuation-in-part of application No. 08/951,550, filed on Oct. 16, 1997, now Pat. No. 5,992,000.

(51) Int. Cl.[7] ................................................. B23P 19/04
(52) U.S. Cl. ........................... 29/234; 29/282; 29/283.5; 29/516; 72/402
(58) Field of Search .................. 29/234, 235, 280, 29/282, 283.5, 516, 517, 240; 606/1.11, 108, 198; 623/1; 72/402, 385

(56) References Cited

U.S. PATENT DOCUMENTS

| 1,863,048 | A | * | 6/1932 | Hayford | 29/517 |
| 2,751,077 | A | * | 6/1956 | Latin et al. | 72/268 |
| 2,887,222 | A | * | 5/1959 | Latin et al. | 72/268 |
| 3,068,563 | A | * | 12/1962 | Reverman | 29/517 |
| 3,149,513 | A | * | 9/1964 | Dollens | 29/517 |

(List continued on next page.)

FOREIGN PATENT DOCUMENTS

| DE | 295 06 654.7 | 7/1995 | A61M/29/00 |
| DE | 195 32 288 A1 | 3/1997 | A61M/29/00 |
| EP | 0 630 623 A2 | 12/1994 | |
| EP | 0 701 800 | 3/1996 | |
| WO | WO 96/03092 A1 | 2/1996 | A61F/2/02 |
| WO | WO 96/38197 | * 12/1996 | 606/198 |
| WO | WO 97/20593 | 9/1997 | A61M/29/00 |
| WO | WO 98/19633 | 5/1998 | A61F/2/06 |

OTHER PUBLICATIONS

Derwent Abstract Accession No. 93-135787/199317, abstract of DE 4235004, 1993.

Primary Examiner—David P. Bryant
Assistant Examiner—Jermie E. Cozart
(74) Attorney, Agent, or Firm—Vidas, Arrett & Steinkraus

(57) ABSTRACT

A stent crimper comprising a plurality of crimping members extending between a first support and a second support. The first and optionally the second supports has an opening therethrough sized to allow a stent therethrough. The first and second supports extend from a base. The crimping members are disposed about the circumference of a circle everywhere along the length of the members. Finally, the flexible members extend through a bore in a die. The die is movable in an axial direction along the flexible members.

15 Claims, 15 Drawing Sheets

U.S. PATENT DOCUMENTS

| | | | | |
|---|---|---|---|---|
| 4,361,948 A | * | 12/1982 | Omata | 29/517 |
| 4,578,982 A | * | 4/1986 | Schrock | 72/402 |
| 4,610,834 A | * | 9/1986 | Baron et al. | 29/235 |
| 5,026,377 A | * | 6/1991 | Burton et al. | 606/108 |
| 5,183,085 A | | 2/1993 | Timmermans | 140/89 |
| 5,261,263 A | * | 11/1993 | Whitesell | 72/402 |
| 5,290,305 A | | 3/1994 | Inoue | 606/191 |
| 5,338,295 A | | 8/1994 | Cornelius et al. | 604/96 |
| 5,381,686 A | | 1/1995 | Thorup | 72/453.06 |
| 5,411,521 A | | 5/1995 | Putnam et al. | 606/225 |
| 5,437,083 A | | 8/1995 | Williams et al. | 29/235 |
| 5,509,184 A | * | 4/1996 | Herrero | 29/282 |
| 5,546,646 A | | 8/1996 | Williams et al. | 29/407 |
| 5,591,222 A | | 1/1997 | Susawa et al. | 623/1 |
| 5,626,604 A | | 5/1997 | Cottone, Jr. | 606/198 |
| 5,628,754 A | | 5/1997 | Shevlin et al. | 606/108 |
| 5,630,830 A | | 5/1997 | Verbeek | 606/198 |
| 5,672,169 A | | 9/1997 | Verbeek | 606/1 |
| 5,700,285 A | | 12/1997 | Myers et al. | 623/1 |
| 5,725,519 A | | 3/1998 | Penner et al. | 606/1 |
| 5,736,251 A | * | 4/1998 | Pinchuk | 606/1 |
| 5,738,674 A | | 4/1998 | Williams et al. | 606/1 |
| 5,746,764 A | | 5/1998 | Green et al. | 606/194 |
| 5,749,921 A | | 5/1998 | Lenker et al. | 623/1 |
| 5,766,203 A | * | 6/1998 | Imran et al. | 606/198 |
| 5,810,871 A | * | 9/1998 | Tuckey et al. | 606/198 |
| 5,810,873 A | | 9/1998 | Morales | 606/198 |
| 5,836,952 A | | 11/1998 | Davis | 606/108 |
| 5,836,965 A | | 11/1998 | Jendersee et al. | 606/198 |
| 5,860,966 A | | 1/1999 | Tower | 606/1 |
| 5,893,852 A | | 4/1999 | Morales | |
| 5,893,867 A | | 4/1999 | Bagaoisan et al. | |
| 5,911,752 A | | 6/1999 | Dustrude et al. | 623/1 |
| 6,082,990 A | * | 7/2000 | Jackson et al. | 29/517 |
| 6,167,605 B1 | | 1/2001 | Morales | 29/282 |

\* cited by examiner

RADIAL STENT CRIMPER

This application is a Continuation-In-Part of U.S. application Ser. No. 08/951,550 filed Oct. 16, 1997 now U.S. Pat. No. 5,992,000, the contents of which are incorporated herein in their entirety by reference.

BACKGROUND OF THE INVENTION

This invention relates to an assembly and a method for fastening a stent onto a catheter. This kind of device finds routine use in the area of percutaneous transluminal coronary angioplasty (PTCA) procedures, although it may be used in other types of procedures, as well.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with the crimping of inflation expandable stents although self-expanding stent may be used as well.

An example of a stent is described in PCT Application NO. 960 3092 A1, published Feb. 8, 1996, the content of which is incorporated herein by reference.

In advancing an inflation expandable balloon through a body vessel to the deployment site, the stent must be able to securely maintain its axial position on the delivery catheter, without trans-locating proximally or distally, and especially without becoming separated from the catheter. Stents that are not properly secured or retained to the catheter may slip and either be lost or be deployed in the wrong location or partially deployed. In securing a stent to a catheter, however, the stent must be crimped in such a way as to minimize or prevent altogether distortion of the stent and to thereby prevent abrasion and/or reduce trauma of the vessel walls.

In the past, crimping has been done by hand often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Recently, stent crimping devices have been disclosed in U.S. Pat. No. 5,546,646 to Williams et al, U.S. Pat. No. 5,183,085 to Timmermans et al., U.S. Pat. No. 5,626,604 to Cottone, Jr., U.S. Pat. No. 5,725,519, to Penner et al., U.S. Pat. No. 5,810,873 to Morales, WO 97/20593 and WO 98/19633.

All US patents and applications all other published documents mentioned anywhere in this application are incorporated herein by reference in their entirety.

BRIEF SUMMARY OF THE INVENTION

The present invention, in one embodiment, is directed to a stent crimper formed of an inner tube and an outer tube, the inner tube movably or slidably disposed in the outer tube. The inner tube has a first end and a slotted second end. The slotted second end comprises a plurality of flexible axially oriented fingers along the tube and is operable from an open configuration in which the fingers flare outward from the tube to a closed configuration. The inner diameter of the inner tube is sized to correspond approximately to the desired diameter of the crimped stent. The inner diameter of the outer tube is sized to substantially correspond to the outer diameter of the inner tube. In use, the fingers of the inner tube are opened, a stent, optionally disposed about a catheter, is placed therein and the outer tube slid over the slotted end of the inner tube.

In another embodiment similar to that described above, the inner diameter of the outer tube is greater than the outer diameter of the inner tube so that the outer surface of the inner tube and the inner surface of the outer tube are not in frictional engagement. The inner and outer tubes are, however, movably secured to one another. The device otherwise operates in the same way as the above described stent crimper. As the outer tube is slid over the slotted end of the inner tube, the fingers close down on the stent and crimp the stent. The stent will be crimped to a diameter approximately equal to the difference between the inner diameter of the outer tube and twice the wall thickness of the inner tube.

The invention is also directed to methods of crimping a stent as described above.

In yet another embodiment, the invention is directed to a stent crimper comprising a first support having an opening therethrough, the opening sized to allow a stent, optionally disposed about a catheter, therethrough and a second support, optionally having an opening therethrough both extending from a base. A plurality of flexible members extend between the first support and the second support. The members are disposed about the circumference of a circle everywhere along the length of the members. The flexible members extend through a bore in a movable die. In use, a stent, optionally disposed about a catheter, is placed in between the flexible members and passed through the bore in the die.

In yet another embodiment, the invention is directed to a method of crimping a stent to a stent delivery catheter using a pressure chamber. A stent disposed about a catheter is inserted in an elastomeric tube in a pressure chamber. The pressure chamber is pressurized collapsing the elastomeric tubing onto the stent and the stent onto the catheter.

In yet another embodiment of the invention, a sleeve is disposed about a stent mounted on a balloon. The balloon is inflated to a predetermined pressure. At the predetermined pressure, tension is applied to the sleeve and the balloon is allowed to deflate slowly. The application of tension to the tube causes the tube to stretch and the diameter to decrease thereby applying a crimping force to the stent. As a result of this method, some of the balloon folds will reside between struts of the stent. The sleeve may also be operated independently of the balloon in crimping the stent.

In another embodiment, the invention is directed to an apparatus and a method for crimping a stent by rolling the stent between two plates which are separated by a distance. The plates may be parallel to one another or disposed at an oblique angle relative to one another.

Another embodiment of the invention is directed to a stent crimper comprising a plurality of offset rotatable cams disposed about a center region. The center region is sized to contain a stent therein. Each cam is in mechanical communication with a cam rotating drive.

Another embodiment of the invention is directed to a stent crimper comprising a fixed roller and a plurality of translatable rollers which are translated, in sequence, to engage the stent and apply a crimping force thereto.

BRIEF DESCRIPTION OF THE SEVERAL VIEWS OF THE DRAWINGS

A detailed description of the invention is hereafter described with specific reference being made to the drawings in which:

FIG. 10b is a schematic illustration of cam assembly 610a from FIG. 10a;

DETAILED DESCRIPTION OF THE INVENTION

Figure 1A:
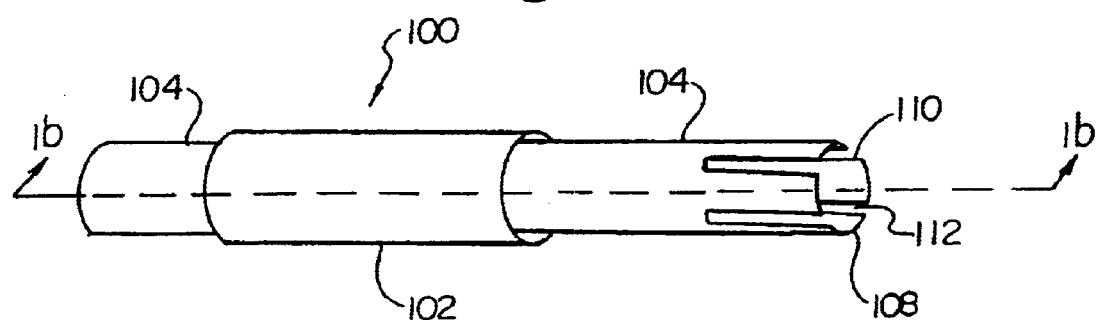
FIG. 1a is a side view perspective of a first embodiment of the radial stent crimper utilizing a tube within a tube arrangement.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable, self-expanding and balloon expandable, or otherwise expandable as are known in the art. Furthermore, where reference is made to crimping a stent, the invention specifically contemplates crimping stents, stent-grafts, grafts and other endoluminal prostheses.

Also, for the purposes of this disclosure, the term 'stent bearing region of a catheter' and similar terms refer to the portion of a catheter tube about which a stent is to be mounted or is mounted. In the case of balloon expandable stents, the terms refer to the portion of the catheter tube and balloon about which the stent is to be mounted or is mounted.

Finally, it is understood that the term 'crimping' and its cognates refer to a reduction in size or profile of a stent. Typically, the diameter of the stent is reduced in size. When reference is made to crimping a stent to a catheter, a balloon may be situated between the stent and the catheter tube or the stent may be crimped to a region of a catheter tube directly. The stent may also be crimped, absent a catheter, within the context of this disclosure, by reducing it in size.

Figure 1B:
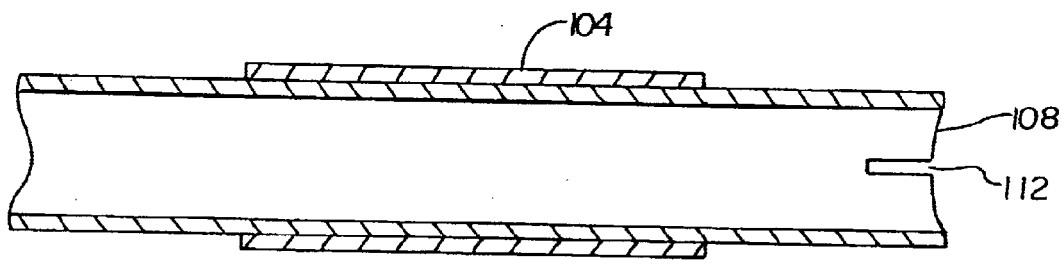
FIG. 1b is a transverse slice of FIG. 1a taken along line 1b—1b.

A first embodiment of the radial stent crimper is shown in FIG. 1a. The crimper, shown generally at 100, comprises an outer tube 102 and an inner tube 104 slidably disposed therein. Inner tube 104 has a first end 106 having a first predetermined outer diameter and inner diameter. The inner diameter is sized approximately to the desired diameter of the stent after crimping. Desirably, the inner diameter of inner tube 104 will be slightly smaller than the desired diameter of the stent to allow for slight recoil of the stent to the desired diameter following crimping. As shown in FIG. 1a and in transverse cross-section in FIG. 1b, the outer diameter of inner tube 104 and the inner diameter of outer tube 102 are sized relative to one another such that the portion of the outer surface of the inner tube which is within outer tube 102 frictionally and movably engages the inner surface of the outer tube. Inner tube 104 may be longer than outer tube 102, as shown in FIG. 1a or shorter than outer tube 102. Inner tube 104 further has a slotted second end 108 comprising a plurality of flexible axially oriented fingers 110 along the tube with slots 112 extending between fingers. Slotted second end 108 is operable from an open configuration in which fingers 110 flare outward to a closed configuration. In the embodiment shown in FIG. 1a, four fingers are present. The stent crimper may be made with additional or fewer fingers. At least two fingers are required. Preferably, the fingers have sufficient length to receive and frictionally engage the entirety of the stent when the stent is placed in the slotted second end.

Figure 2:
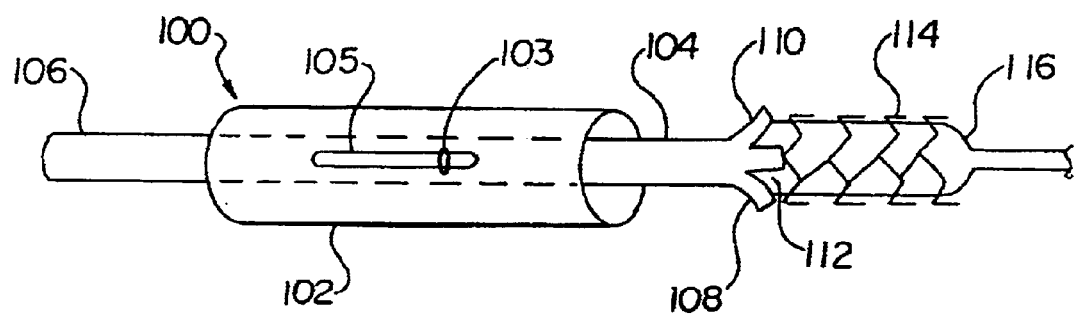
FIG. 2 is a side view perspective of the embodiment shown in FIG. 1c showing the engagement of a catheter mounted stent with the fingered portions of the inner tube.

In use, fingers 110 are spread apart, and stent 114, optionally disposed about catheter 116, is inserted in slotted second end 108 of inner tube 104 and outer tube 102 slid thereover uniformly collapsing fingers 110 onto stent 114, as shown in FIG. 2.

Figure 1C:
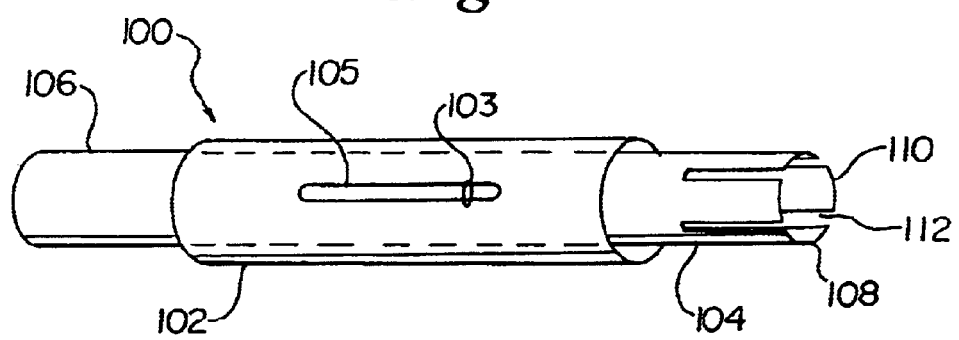
FIG. 1c is a side view perspective of a first embodiment of the radial stent crimper utilizing a tube within a tube arrangement.

In another embodiment, as shown in FIG. 1c, the outer diameter of inner tube 104 is sufficiently smaller than the inner diameter of outer tube 102 that the inner surface of outer tube 102 does not frictionally engage the outer surface of inner tube 104. In this embodiment, inner tube 104 is desirably movably secured to outer tube 102 via appendage 103 which extends from inner tube 104 through channel 105 in outer tube 102. Other suitable securement devices may also be used to movably secure the inner and outer tubes.

The stent crimper of FIG. 1c will crimp a stent to a diameter substantially equal to the difference in length between the inner diameter of the outer tube and the twice the wall thickness of the inner tube.

The present invention is also directed to a method of crimping a stent with the slotted stent crimpers as described above.

Figure 3:
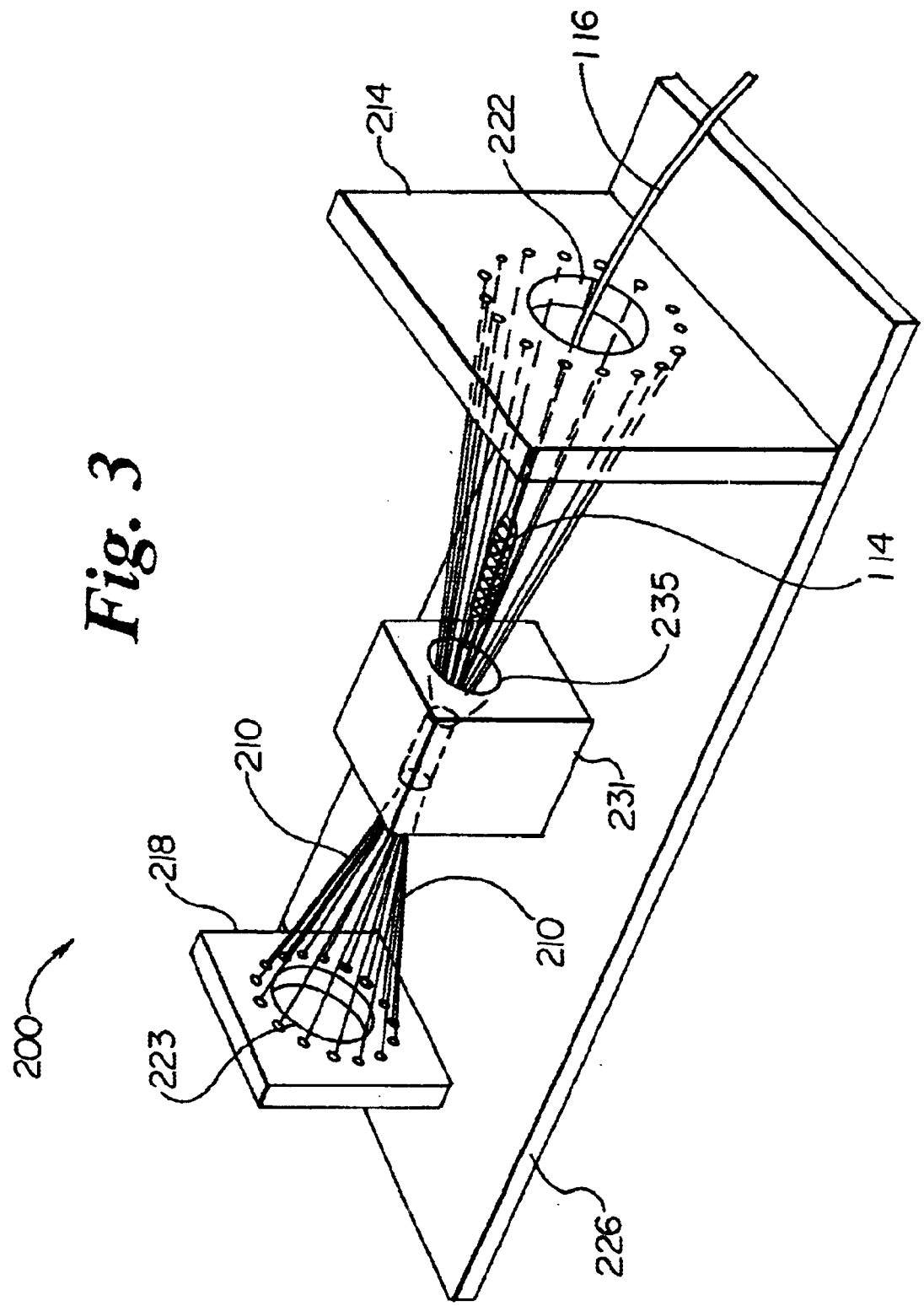
FIG. 3 is a second embodiment of the inventive radial stent crimper wherein a plurality of flexible wires and a crimping die are utilized to uniformly crimp the stent.

In another embodiment of the present invention, as depicted in FIG. 3, a stent crimper, shown generally at 200, utilizes a plurality of uniformly spaced crimping members 210 to apply a radially inward crimping force to a stent.

Crimping members 210 are attached at a first end to a first support 214 and at a second end to a second support 218. Crimping members 210 are arrayed to form a frustoconical shape—at every point along the length of members 210, the plurality of members are arranged about a circle. The embodiment shown in the FIG. 3 includes 12 crimping members 210. Fewer members may be used or additional members may be used.

First support 214 has an opening 222 therethrough sized to allow stent 114, optionally disposed about catheter 116, therethrough. Optionally, second support 218 also has an opening 223 therethrough sized to allow stent 114, optionally disposed about catheter 116, therethrough.

First support 214 and second support 218 are desirably anchored together via base member 226. First and second supports 214 and 218 and base member 226 may be made of any suitable material including wood, metal or plastic.

Figure 4:
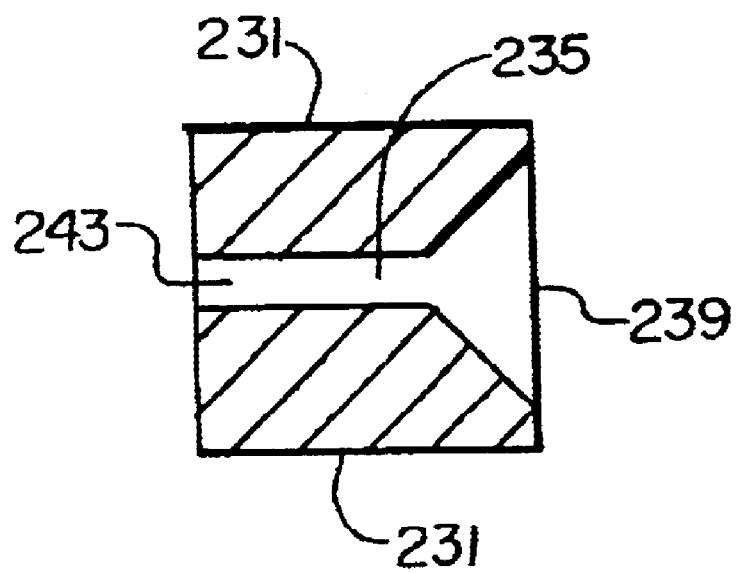
FIG. 4 is a cross-sectional view of the crimping die shown in FIG. 3.

Finally, crimper 200 comprises a crimping die 231 slidably mounted about crimping members 210. Die 231 has a bore 235 therethrough. Bore 235, shown in greater detail in FIG. 4 is circular in cross-section along its entire length and includes a tapered portion 239 and a non-tapered portion 243. The invention also contemplates the use of a die having a bore of constant radius, the use of a die having a constantly tapering bore and the use of a die having a bore which is tapered at both ends and of constant diameter in between the ends.

Crimping members 210 may be made of wire or fiber (including polymeric fibers) or any other suitable material. Crimping members 210 are desirably made of a bendable material so that as die 231 slides along the members, the members will bend inward and transmit the crimping force to the stent.

Optionally, crimping members 210 may be textured or coated to increase the friction between the crimping members and the stent. This allows the crimping member to better grip the stent as the crimping die approaches the stent and prevents the stent from slipping away from the approaching crimping die. The crimping members may alternatively be coated with a lubricious coating to minimize trauma to the stent.

Die 231 may be made of any material harder than the stent and crimping members to ensure that the stent is crimped rather than the die being deformed. One material suitable for use is stainless steel. Other metals and/or polymeric materials may be used in lieu of stainless steel.

In use, stent 114 is disposed about a stent bearing region of catheter 116 and inserted through opening 222 and interior to crimping members 210. Die 231 is slidably moved along crimping members 210 toward first support 214 drawing crimping members 210 inward. The die is oriented such that the stent first enters the tapered portion. As crimping die 231 passes over stent 114, die 231 and crimping members 210 will crimp the stent. After passing over the entire length of the stent, the crimping die may optionally be drawn back toward second support 218 and the crimped stent removed through bore 222. The stent may also be removed through opening 223.

Figure 5:
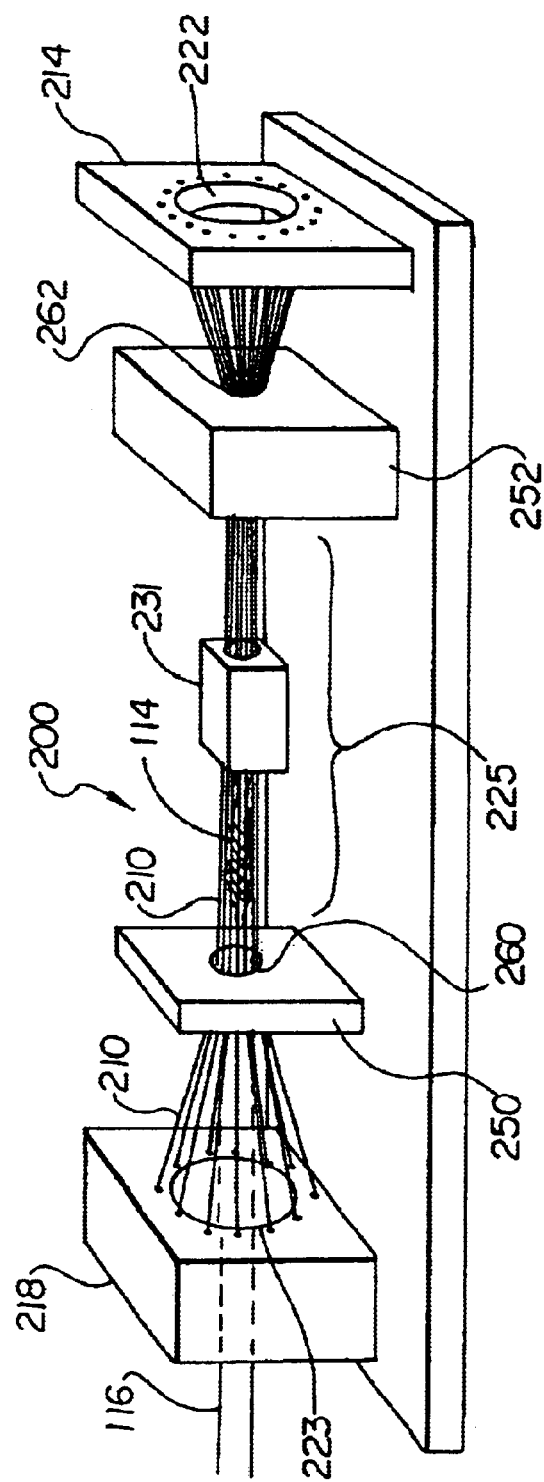
FIG. 5 is an alternative embodiment of the stent crimper shown in FIG. 3 wherein the wires are collimated in a central region.

In another embodiment, as shown generally at 200 in FIG. 5, the crimper shown in FIG. 3, further includes a first restriction member 250 with a restriction bore 260 therethrough and a second restriction member 252 with a restriction bore 262 therethrough. The diameters of restriction bores 260 and 262 are substantially the same and greater than the diameter of the stent to be crimped. Crimping members 210 pass through restriction bores 260 and 262 and are collimated in region 225 between first and second restriction members 250 and 252 so that crimping members 210 are positioned substantially parallel to one another in region 225.

Restriction bores 260 and 262 may incorporate a design similar to bore 235 of crimping die 231, as shown in FIG. 4 including a tapered region where the crimping members are initially restricted from their greater arrayed diameter at the first and second ends respectively.

In use, a stent (or stents) is inserted through opening 222 or opening 223, and positioned in between restriction members 250 and 252 in collimated region 225. Crimping die 231 is passed over stent 114 thereby crimping the stent.

Figure 6:
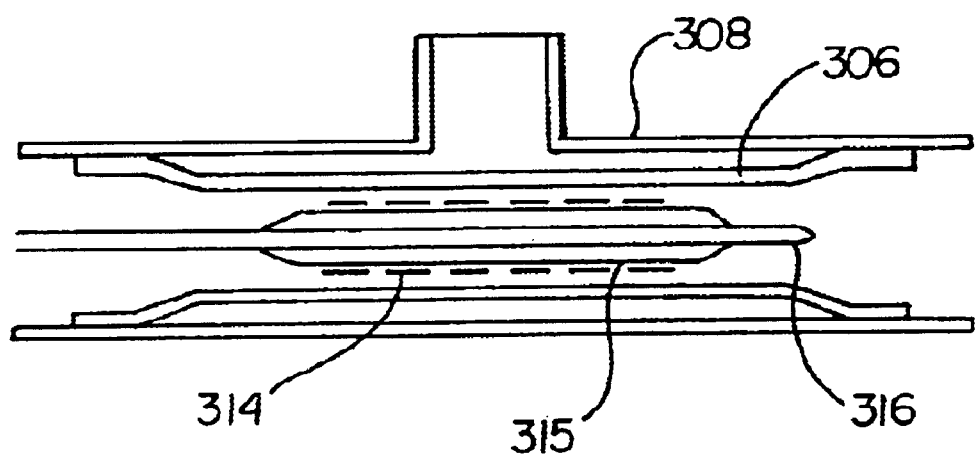
FIG. 6 is a cross-sectional view of a pressure vessel with a stent therein.

Another embodiment of the invention is directed to a method of uniformly crimping a stent utilizing a pressure chamber. As shown in FIG. 6, stent 314 is disposed about an inflatable medical balloon 315 mounted on catheter 316 and placed in an elastomeric tube or membrane 306. Tube 306 along with stent 314 and catheter 316 are then placed in pressure chamber 308 and the chamber pressurized. The pressure in the chamber collapses elastomeric tube 306 onto stent 314 and stent 314 onto balloon 316. The catheter and stent may then be removed from the chamber.

Suitable materials for the tube or membrane include balloon material as is known in the art.

The pressure inside the pressure chamber should be sufficient to cause the tubing to collapse inward toward the stent and apply a radially inward crimping force to crimp the stent to the catheter. Using this technique, a stent may be uniformly crimped without being subjected to the mechanical forces associated with other crimping techniques.

Figure 7:
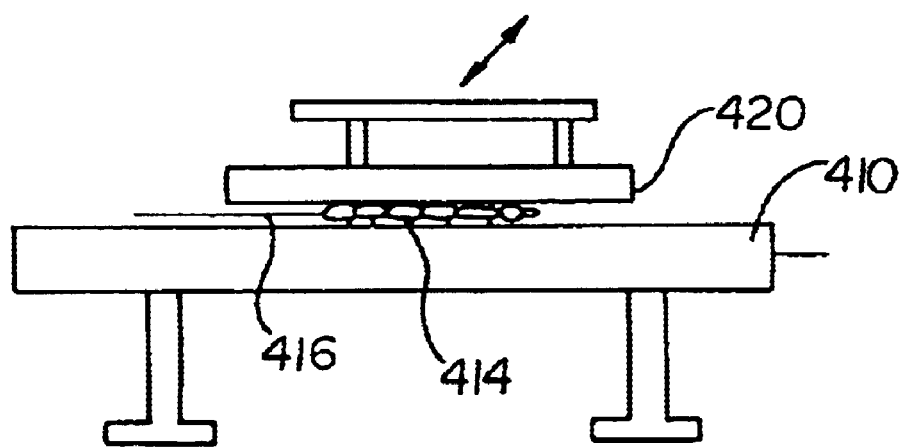
FIG. 7 is a front view of an apparatus for crimping a stent via rolling.

In yet another embodiment, the invention is directed to an apparatus and a method for crimping a stent in which the stent is placed on a flat surface such as a steel plate and a second flat surface, at least as wide as the stent, is placed over the stent. As shown in FIG. 7, a front view of a apparatus for crimping a stent, second flat surface 420 is moved relative first flat surface 410 so as to roll stent 414 along its circumference while applying a pressure thereto, thereby reducing the stent in size. The direction of rolling will be into the page. Desirably, as shown in FIG. 7, stent 414 will be disposed about catheter 416 and crimped thereto via this method. The method may be used by itself or in conjunction with any of the other methods disclosed herein to either precrimp a stent or crimp a precrimped stent.

Figure 8:
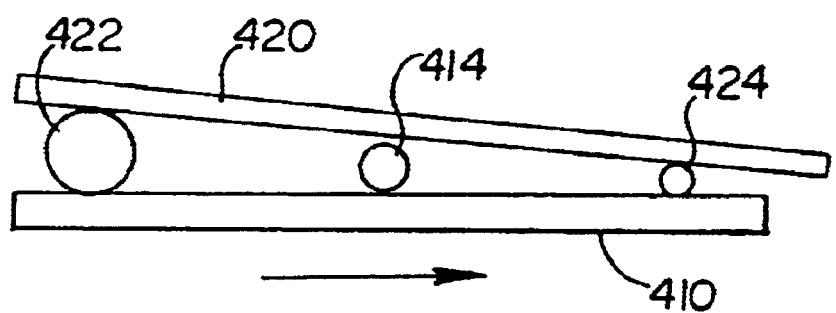
FIG. 8 is a side view of an apparatus for crimping a stent via rolling.

The second plate may either be held parallel to the first plate, as shown in FIG. 7 or may be at an oblique angle relative to the first plate as shown in FIG. 8. In the latter case, the spacing between first plate 410 and second plate 420 varies and the stent is rolled from a region of greater separation between the plates to a region of lesser separation between the plates to crimp the stent. FIG. 8 is a side view of an apparatus. The second plate is moved in the direction of the arrow.

Desirably, second plate 420 will be supported by at least two supports. As shown in FIG. 8, first support 422 and second support 424 are provided in the form of rollers of differing diameters to facilitate sliding of the upper plate relative to the lower plate. The diameter of the crimped stent is determined by the separation of the first and second plates at the second support 424.

In another embodiment of the invention, at least one of the first and second plates of the embodiments of FIGS. 7 and 8 may be replaced by a continuous belt.

The invention also contemplates the use of an additional protective sleeve, desirably in braid form, with a pick count of between about 20 and 90 picks/inch and preferably about 55 picks/inch, to prevent direct contact between the stent and the crimping device. This may minimize or eliminate any marring or nicking of the stent by the crimping member. A suitable sleeve comprised of polymeric tubing is described in copending, commonly assigned U.S. application Ser. No. 08/951,550. In addition to the materials disclosed therein for the sleeve, the sleeve may be formed of polyester, polyamide, nitinol, kevlar, polypropylene or polyurethane.

In addition to protecting the stent, the protective sleeve may also be used to reduce the stent in size prior to the stent being crimped as described in U.S. application Ser. No. 08/951,550. To that end, in another embodiment of the invention, a stent, disposed about a balloon, is inserted in a sleeve, desirably a polymeric braid. The balloon is inflated to a desired pressure. At the desired pressure a tension is applied to the sleeve and the pressure slowly released from the balloon. As the balloon deflates, the stent is crimped, via the sleeve, onto the balloon, allowing some of the balloon folds in between the struts of the stent. This method may be used by itself or in conjunction with any other crimping method including those disclosed herein.

This latter method allows at least a portion of the stent to be crimped to a smaller diameter than the balloon. This form of crimping—recoil crimping, results in the balloon recoiling or pushing outward on the stent. The modulus of the stent material resists this outward pressure increasing the friction between the balloon and stent surface. Recoil crimping may also be achieved by non-uniformly crimping a stent.

In a related embodiment, increased stent securement may also be achievable by inflating a balloon so that portions of the balloon extend through the openings in a stent, heat setting the stent geometry into the balloon and then crimping the balloon using one of the above techniques.

Improvements in stent retention may also be achieved by crimping a stent to a balloon and catheter where the balloon is oversized or unfolded proximal and/or distal to the stent. Similarly, partially inflating the balloon and heat setting the cone portions in an at least partially expanded stated in conjunction with crimping may increase stent retention.

Figure 9:
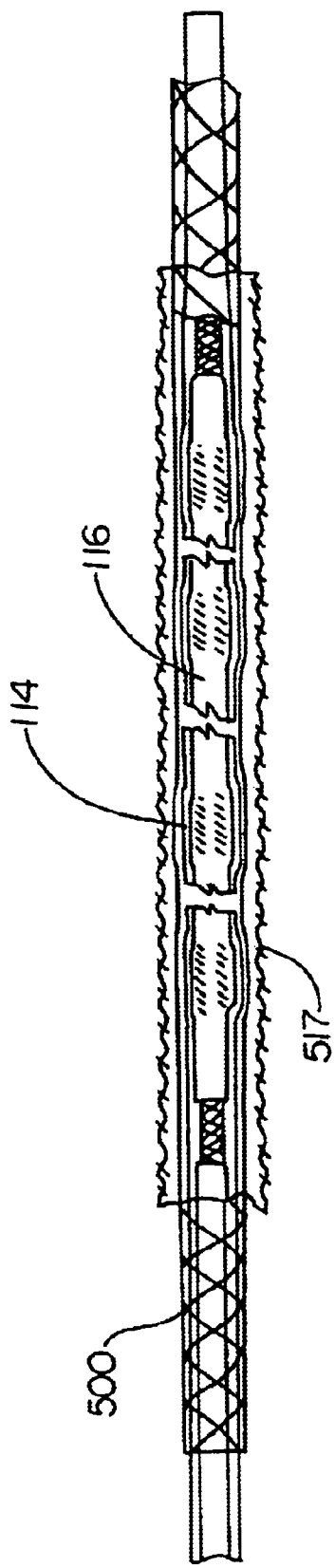
FIG. 9 is a side view of a stent disposed about a catheter with an additional stent securement tube thereon.

Improvements in stent retention may also be achieved by crimping a stent to a catheter using a reducible diameter tube or braid as disclosed above or any of the other techniques disclosed herein and then loading an additional tube over the crimped stent. The additional tube helps maintain the stent in its crimped state. Desirably, the additional outer tube will itself be made of a compressive material to apply a further crimping force to the stent. The additional outer tube is removed prior to using the catheter. The combination of catheter, braid and additional outer tube in accordance with this aspect of the invention is shown in FIG. 9. Nylon braid 500 is crimped disposed about stent 114 and catheter 116. Additional outer tube 517 is disposed about braid 500.

Figure 10A:
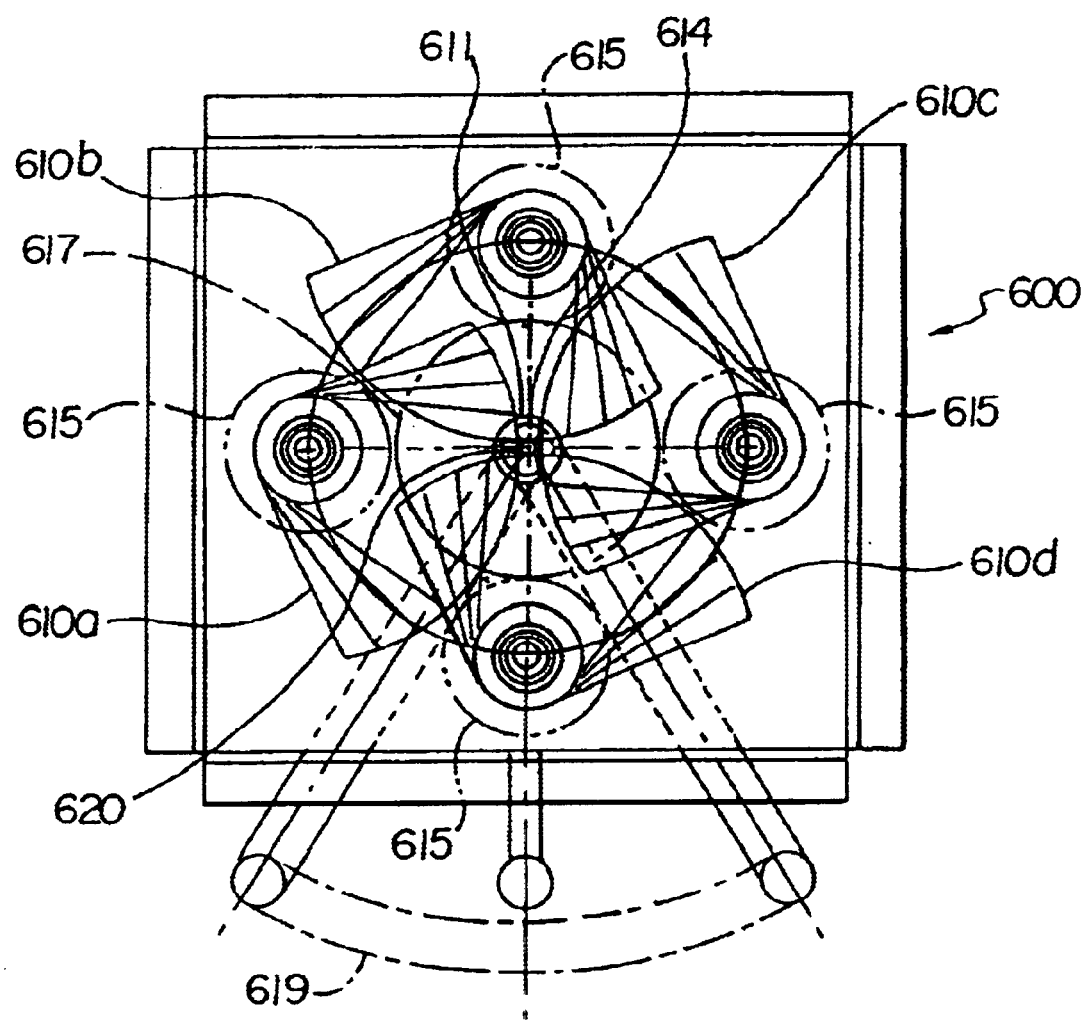
FIG. 10a is a schematic illustration of a cam-based stent crimper.
Figure 10B:
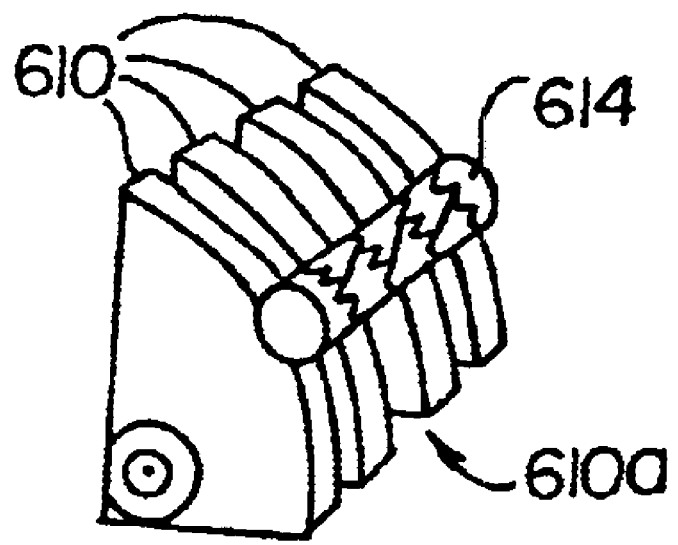
Figure 10C:
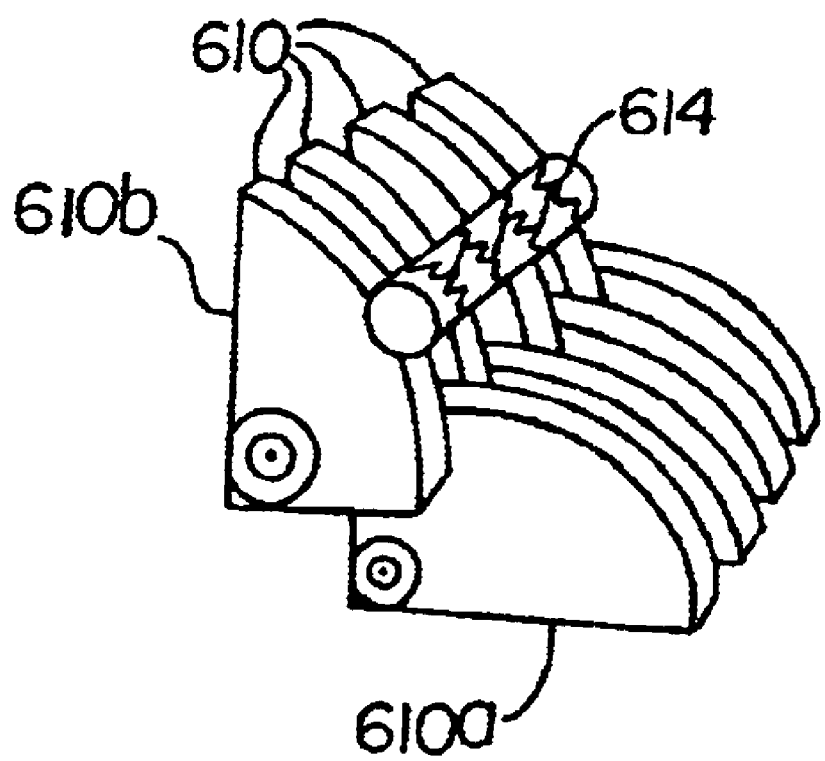
FIG. 10c is a schematic illustration of two intermeshed cam assemblies.

In yet another embodiment, the invention is directed toward a stent crimper which relies on cams to crimp a stent. As shown in FIG. 10a, a stent crimper, shown generally at 600, is formed of four assemblies of longitudinally offset, rotatable cams 610a–d disposed about a center region 611 which contains a stent holder 620. Each assembly of cams contains one or more cams 610. FIG. 10b shows an assembly of cams in which four cams 610 are present. The exact number of cams will depend on the length of the stent to be crimped and the width of each cam. Desirably, the number of cams and width of the cams will be chosen such that the cams extend over the entire length of the stent to be crimped. Cam assemblies 610a and 610c are disposed opposite one another as are cam assemblies 610b and 610d. Cam assemblies 610a and 610c are offset along the length of the stent from cam assemblies 610b and 610d such that the individual cams in cam assemblies 610a and 610c mesh with the individual cams in cam assemblies 610b and 610d. The meshing is shown in partial detail in FIG. 10c. For the sake of clarity, stent 614 is shown slightly displaced from the center region in FIG. 10c. Each cam 610 is driven by a spur gear 615 which in turn is driven by antibacklash gear 617. Antibacklash gear 617 is in communication with actuation device 619, shown in part in FIG. 10a. Actuation device 619 may be a lever or any other suitable device for rotating antibacklash gear 617. Finally, center region 611 is sized to contain stent 614, optionally disposed about a catheter.

In use, a stent, optionally disposed about a catheter, is placed on stent holder 620. Actuation device 619 is rotated thereby rotating antibacklash gear 617. Antibacklash gear 617 in turn rotates each of spur gears 615 causing cams 610 to rotate into center region 611 and thereby apply a crimping force to the stent. As each cam rotates, it applies a crimping force to the stent. The rotation of the cams causes stent 614, in contact with the cams, to rotate as well, thereby ensuring a uniform crimp.

The invention also contemplates embodiments which use additional or fewer cam assemblies. In an embodiment having six cams, three sets of two opposing cams would be disposed about a center region.

Figure 11:
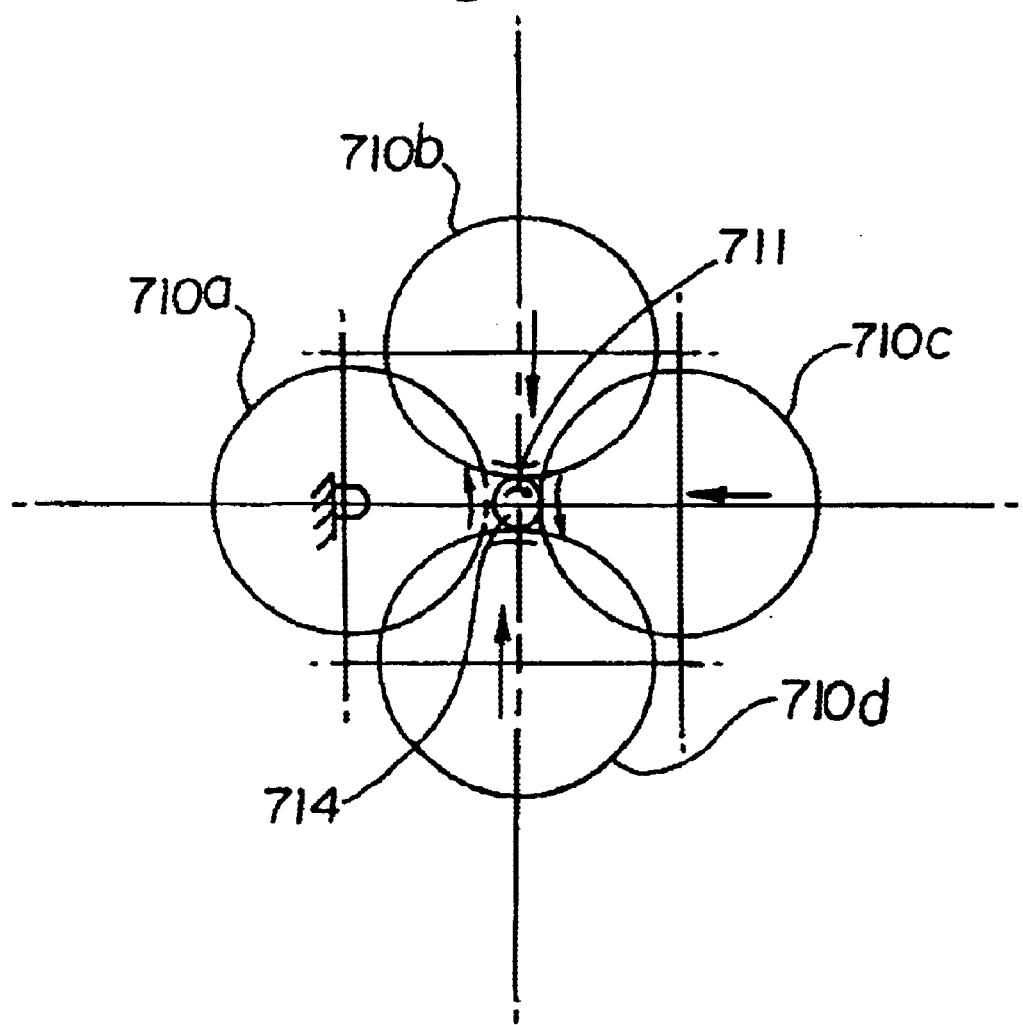
FIG. 11 is a schematic illustration of a roller-based stent crimper.

In yet another embodiment of the invention, illustrated in FIG. 11, the crimper is made of four rollers 710a–d. Roller 710a is fixed while rollers 710b–d are movably mounted so that they can engage stent 714 in center region 711. Each rollers is mounted about it center. In operation, each of rollers 710b–d in succession is moved toward the stent, engages stent 714 thereby applying a crimping force to the stent and then disengages stent 714 and is moved away from the stent. The stent is effectively rolled down in size to a desired, crimped diameter. The extent of the crimping is controlled by the force transmitted by the rollers which engage the stent.

Although FIG. 11 depicts four rollers, the invention also contemplates embodiments with a single fixed roller and a single translatable roller and more generally, embodiments with a plurality of translatable rollers.

A similar crimper may be constructed by substituting eccentric rollers for rollers 710b–d. In so doing, the need for linearly movable rollers is eliminated. Of course, the eccentricities of the rollers and the order of stent engagement must be chosen to avoid interference between adjacent rollers.

The invention is also directed to a method of crimping a stent to a catheter in which crimping is effected by sequentially engaging the stent with different crimping members. Specifically, a stent crimper comprising a plurality of movable crimping members disposed about a catheter receiving region is provided. Each crimping member is capable of being moved into the catheter receiving region. A stent disposed about a stent bearing portion of a catheter is inserted into the catheter receiving region of the stent crimper. Each crimping member is sequentially moved into engagement with the stent thereby applying a crimping force to a desired portion of the stent and then removed from the catheter receiving region and engagement with the stent.

Typically, in the practice of the inventive method, the crimping members will be rotatable cams which may be rotated into the catheter receiving region. Other crimping members may also be used such as dies of various shapes, the choice of dies tailored to the particular crimping to be done. Desirably, a die having a groove cut therein to accommodate the stent may be employed.

The catheter and stent may be reside in the catheter receiving region or may be moved or slid into the region using a suitable stent moving device.

The invention is further directed to methods of crimping in which any of the individual crimping modalities disclosed herein is combined in sequence with any other crimping modality disclosed herein and/or with any of the crimping modalities described in the commonly assigned, cofiled U.S. patent applications Ser. Nos. 09/401,467, 09/401,213 and 09/401,218, and commonly assigned and copending U.S. application Ser. No. 08/951,550 all of which are directed to stent crimpers and all of which are incorporated herein in their entirety by reference. Thus, a stent may be pre-crimped using one crimping technique and further crimped using another crimping technique.

This completes the description of the preferred and alternate embodiments of the invention. Those skilled in the art may recognize other equivalents to the specific embodiment described herein which equivalents are intended to be encompassed by the claims attached hereto.

In addition to being directed to the specific combinations of features claimed below, all possible alternative dependent combinations of the features recited above or in the dependent claims, whether written in multiple dependent form or not, should be considered to be within the scope of the invention.

What is claimed is:

1. A device for reducing the cross-section of a stent, the device comprising a plurality of rotatable crimping members driven via a central gear and disposed in fixed locations about a center region, the center region having a longitudinal axis substantially orthogonal to a plane of rotation defined by the rotation of the plurality of rotatable crimping members, the central gear and each of the crimping members having planes of rotation substantially coplanar with or parallel to one another, each crimping member constructed and arranged such that a portion of each crimping member is capable of rotating into the center region and crimping at least a portion of a stent.

2. The device of claim 1 comprising at least four crimping members.

3. The device of claim 1 further comprising a stent in the center region.

4. The device of claim 1 wherein the crimping members are longitudinally offset from one another along the length of the stent.

5. The device of claim 1 wherein each crimping member is in mechanical communication with an actuation device.

6. The device of claim 1 wherein each of the crimping members has a curved face, a portion of which extends into the center region.

7. The device of claim 1 wherein each of the crimping members is pie shaped.

8. The device of claim 7 further comprising a stent disposed in the center region.

9. The device of claim 8 wherein the crimping members are longitudinally offset from one another along the length of the stent.

10. The device of claim 1 wherein the portion of the stent crimped is crimped in a substantially uniform manner along the full length of the stent.

11. A device for reducing the cross-section of a stent, the device comprising a plurality of rotatable crimping members driven via a central gear and disposed in fixed locations about a center region orthogonal to a plane of rotation defined by rotation of the plurality of rotatable crimping members, each crimping member having a plane of rotation substantially coplanar with or parallel to the plane of rotation of the other crimping members, each crimping member rotatable such that a portion of the crimping member rotates into the center region thereby crimping at least a portion of the stent, each crimping member in mechanical communication with the central gear via a spur gear.

12. A device for reducing the cross-section of a stent, the device comprising a plurality of crimping members driven via a central gear and disposed in fixed locations about a center region sized to receive a stent when placed longitudinally orthogonal to a plane of rotation defined by the rotation of the crimping members, each crimping member in mechanical communication with the central gear via a spur gear and rotatable such that a portion of the crimping member rotates into the center region thereby crimping at least a portion of the stent.

13. A device for reducing the cross-section of a stent, the device comprising a plurality of rotatable crimping members disposed in fixed locations about a center region and driven via a central gear, the center region sized to receive therein a stent having a longitudinal axis, the stent being oriented such that the stent's longitudinal axis is parallel to the axis of rotation of the rotatable crimping members, the crimping members longitudinally offset from one another and constructed and arranged such that a portion of each crimping member is capable of rotating into the center region and crimping at least a portion of a stent.

14. A device for reducing the cross-section of a stent, the device comprising a plurality of rotatable crimping members disposed in fixed locations about a center region having a void space having a size and driven via a central gear, each crimping member rotatable such that a portion of the crimping member is capable of rotating into the center region and reducing the size of the void space of the center region, the center region oriented such that the longitudinal axis of the center region is substantially parallel to the axis of rotation of each crimping member.

15. A device for reducing the cross-section of a stent, the device comprising a plurality of crimping members disposed about a center region, the center region substantially encompassed by the crimping members and having a longitudinal axis, the center region arranged such that a radial line extending from the center region to the outside of the device intersects multiple crimping members both in an opened position and a crimping position, each crimping member constructed and arranged such that a portion of each crimping member is capable of crimping at least a portion of a stent and rotating into the center region without contacting crimping members which are adjacent thereto.

* * * * *